(12) United States Patent
Kerkhoffs et al.

(10) Patent No.: US 12,303,678 B2
(45) Date of Patent: May 20, 2025

(54) BLOOD PUMP

(71) Applicant: Abiomed Europe GmbH, Aachen (DE)

(72) Inventors: Wolfgang Kerkhoffs, Aachen (DE); Marius Grauwinkel, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 285 days.

(21) Appl. No.: 17/637,264

(22) PCT Filed: Sep. 1, 2020

(86) PCT No.: PCT/EP2020/074371
§ 371 (c)(1),
(2) Date: Feb. 22, 2022

(87) PCT Pub. No.: WO2021/043776
PCT Pub. Date: Mar. 11, 2021

(65) Prior Publication Data
US 2022/0288379 A1  Sep. 15, 2022

(30) Foreign Application Priority Data
Sep. 2, 2019 (EP) ..................................... 19194971

(51) Int. Cl.
*A61M 60/13* (2021.01)
*A61M 60/221* (2021.01)
(Continued)

(52) U.S. Cl.
CPC .......... *A61M 60/13* (2021.01); *A61M 60/221* (2021.01); *A61M 60/237* (2021.01);
(Continued)

(58) Field of Classification Search
CPC .............. A61M 60/422; A61M 60/237; A61M 60/216; A61M 60/414; A61M 60/178;
(Continued)

(56) References Cited

U.S. PATENT DOCUMENTS

| 6,053,705 A | 4/2000 | Schob et al. |
| 2003/0146157 A1 | 8/2003 | Lueptow |
| 2010/0234941 A1 | 9/2010 | Finocchiaro et al. |

FOREIGN PATENT DOCUMENTS

| CN | 205322884 U | 6/2016 |
| CN | 107355417 A | 11/2017 |

(Continued)

OTHER PUBLICATIONS

International Search Report and Written Opinion for application No. PCT/EP2020/074371 dated Dec. 3, 2020, 13 pp.

(Continued)

*Primary Examiner* — Deborah L Malamud
(74) *Attorney, Agent, or Firm* — Botos Churchill IP Law LLP

(57) ABSTRACT

An intravascular blood pump for percutaneous insertion into a patient's blood vessel is provided. The blood pump comprises a pump casing and an impeller arranged in the pump casing. The blood pump further comprises a drive unit for rotating the impeller, the drive unit comprising a plurality of posts. Each of the posts has an impeller-side end pointing towards the impeller with a front surface facing the impeller. A coil winding is disposed around each of the posts so as to create magnetic field lines running through the front surface of each of the posts. The front surface of at least one of the posts comprises a concavity in which the front surface is inclined downwards towards a central area of the front surface so as to concentrate at least a part of the magnetic field lines running through the front surface.

17 Claims, 12 Drawing Sheets

(51) Int. Cl.
*A61M 60/237* (2021.01)
*A61M 60/422* (2021.01)
*A61M 60/82* (2021.01)
*A61M 60/824* (2021.01)

(52) U.S. Cl.
CPC .......... *A61M 60/422* (2021.01); *A61M 60/82* (2021.01); *A61M 60/824* (2021.01)

(58) Field of Classification Search
CPC .............. A61M 60/419; A61M 60/508; A61M 60/825; A61M 60/808; A61M 60/538; A61M 60/804; A61M 2205/3334; A61M 60/82; A61M 60/896; A61M 60/806; A61M 60/81; A61M 60/88; A61M 60/515; A61M 60/205; A61M 60/416; A61M 2205/3365; A61M 60/122; A61M 60/226; A61M 2205/04; A61M 2205/103; A61M 2210/12; A61M 60/835; A61M 60/855; A61B 5/02141; A61B 5/4836
See application file for complete search history.

(56) References Cited

FOREIGN PATENT DOCUMENTS

| | | |
|---|---|---|
| CN | 107659006 A | 2/2018 |
| EP | 1186310 A1 | 3/2002 |
| RU | 2744482 C1 | 3/2021 |
| WO | 2006047499 A2 | 5/2006 |
| WO | 2017162619 A1 | 9/2017 |
| WO | 2019057636 A1 | 3/2019 |

OTHER PUBLICATIONS

Office Action from corresponding Israeli Patent Application No. 289967 dated Jul. 3, 2024 (3 pp.).
Office Action and Search Report issued in Chinese Patent Application No. 202080061726.X dated Dec. 20, 2024 (24 pp.).

BLOOD PUMP

CROSS-REFERENCE TO RELATED APPLICATIONS

The present application is a national phase entry under 35 U.S.C. § 371 of International Application No. PCT/EP2020/074371, Sep. 1, 2020, published as International Publication No. WO 2021/043776 A1, which claims the benefit of the filing date of European Patent Application No. 19194971.8 filed Sep. 2, 2019, the disclosures of which are hereby incorporated by reference.

This invention relates to an intravascular blood pump, in particular an intravascular blood pump for percutaneous insertion into a patient's blood vessel, to support a blood flow in a patient's blood vessel. The blood pump has an improved drive unit.

BACKGROUND OF INVENTION

Blood pumps of different types are known, such as axial blood pumps, centrifugal (i.e. radial) blood pumps or mixed-type blood pumps, where the blood flow is caused by both axial and radial forces. Intravascular blood pumps are inserted into a patient's vessel such as the aorta by means of a catheter. A blood pump typically comprises a pump casing having a blood flow inlet and a blood flow outlet connected by a passage. In order to cause a blood flow along the passage from the blood flow inlet to the blood flow outlet, an impeller or rotor is rotatably supported within the pump casing, with the impeller being provided with blades for conveying blood.

Blood pumps are typically driven by a drive unit, which can be an electric motor. For instance, WO 2017/162619 A1 discloses an intravascular blood pump having an impeller which is magnetically coupled to an electric motor. The impeller comprises magnets which are disposed adjacent to electrically magnetized zones in the electric motor. Due to attracting forces between the magnets in the impeller and electrically magnetized zones in the motor, rotation of the motor is transmitted to the impeller. That is, the drive unit has a plurality of static posts arranged about the axis of rotation of the impeller, and each post carries a wire coil winding and acts as a magnetic core. A control unit sequentially supplies a voltage to the coil windings to create a rotating magnetic field by which the magnetically coupled impeller is rotated.

More specifically, the intravascular blood pump in WO 2017/162619 A1 comprises a pump casing with a blood flow inlet and a blood flow outlet, an impeller and a drive unit for rotating the impeller. By rotation of the impeller about an axis of rotation and inside of the pump casing, blood can be conveyed from the blood flow inlet to the blood flow outlet by blades of the impeller. The drive unit comprises six posts and a back plate connecting rear ends of the posts to act as a yoke. The posts are arranged in a circle around the axis of rotation, as seen in a plane which is perpendicular to the axis of rotation, wherein each of the posts has a longitudinal axis, which is parallel to said axis of rotation. The posts each have a shaft and an inclined head portion at the impeller-side end of the shaft pointing towards the impeller, the head portion extending radially beyond the shaft so as to form a shoulder which can act as an axial stop for a coil winding disposed around each of the posts. A control unit sequentially supplies a voltage to the coil windings to create a rotating magnetic field. The impeller comprises a magnetic structure which is arranged to interact with the rotating magnetic field such that the impeller follows its rotation.

In operation, neighboring posts may have different magnetization. As a result thereof, magnetic flux running through the posts tends to flow between those neighboring posts in avoidance of the impeller. Such magnetic flux is lost for the generation of torque. A disadvantage of the state of the art is that the head portions extending radially beyond the shafts have a particularly small distance to each other. Accordingly, there is a considerable parasitic magnetic flux between the head portions, which is lost for the generation of torque. While such parasitic flux can be countered by placing magnetically insulating material, such as magnets, between the head portions, the available space is extremely limited and the polarization of the magnets would have to change cyclically in order to achieve a reasonable insulation, which is difficult. It is an objective of the invention to improve the drive unit in this regard.

SUMMARY OF THE INVENTION

The blood pump of the present invention may correspond to the afore-mentioned blood pump. Accordingly, it may be an axial blood pump or a diagonal blood pump, which pumps partly axially and partly radially (the diameter of pure centrifugal blood pumps is usually too large for intravascular applications). However, according to one aspect of the invention, a front surface of the impeller-side end of at least one of the posts—preferably of each of the posts—comprises a concavity in which the front surface is inclined downwards towards a central area of the front surface so as to concentrate at least a part of the magnetic field lines running through the front surface.

Magnetic field lines of magnetic flux exiting from and entering into a surface of a component made of magnetic material run perpendicularly to the surface, i.e. they exit and enter the surface plane vertically. By providing the front surface of a post with a concavity, i.e. with a depression having areas in which the front surface is inclined downwards towards a center of the front surface, the magnetic field lines which are running into and out of the post through the front surface are forced to run closer towards the central axis of the post. As a result, since magnetic field lines never cross each other, they are concentrated in front of the impeller-side end of the post and directed towards the impeller as a bundle. Parasitic flux between neighboring posts is thereby reduced.

The inclination of the concavity is less than 90°, preferably between 0° and 30°, relative to the surface plane.

Preferably, the concavity extends up to a circumference of the front surface. In other words, the concavity may start out from an outer border of the front surface. This has the effect that also the outermost magnetic field lines are affected by the inclination of the concavity. The outermost magnetic field lines are the ones which have the greatest tendency of bridging over to a neighboring post. Therefore, the concavity is most effective if it extends up to the circumference of the front surface of the post.

It may be sufficient that the concavity extends up to the circumference of the front surface of the post on at least two, preferably exactly two, opposite sides of the front surface, namely on those sides which are closest to the neighboring posts. This may be advantageous particularly when the posts are e.g. cylindrically and, thus, circular in cross section. That is, the danger that magnetic field lines bridge over to neighboring posts is the greatest where the posts have little distance from each other. Therefore, the concavity is sufficiently effective if it extends up to the circumference of the front surface of the post only on the two sides which are positioned closest to the respective neighboring posts.

Nevertheless, it is preferred that the circumference of the concavity coincides with the circumference of the front surface. This way, due to the inclination of the concavity, the outermost magnetic field lines are directed towards the center of the front surface along the entire circumference of the front surface. As mentioned, the outermost magnetic field lines are the ones which have the greatest tendency of turning away in avoidance of the impeller. Therefore, the concavity is most effective if its circumference coincides with the circumference of the front surface.

The concavity may have a flat bottom, as it may be sufficient to direct the outermost magnetic field lines towards the center. Thus, at least a region at the circumference of the concavity is downwardly inclined. In this case, the concavity may have a straight-lined inclined side wall when viewed in a cross-sectional plane running vertically through the front surface or it may have a curved inclined side wall when viewed in a cross-sectional plane running vertically through the front surface. A curved inclined side wall having an inclination which increases towards the circumference of the concavity has the effect that the bundling effect on the outermost magnetic field lines is maximal.

Alternatively, the concavity may have a curved cross section with a curved bottom, rather than a flat bottom, when viewed in a cross-sectional plane running vertically through the front surface. This way, the centering effect on the magnetic field lines gradually decreases from the circumference of the concavity towards a center thereof.

Further alternatively, the concavity may have a triangular cross section when viewed in a cross-sectional plane running vertically through the front surface. This way, the maximum depth of the concavity may be increased. The deeper the concavity, the greater the distance is between the respective portion of the front surface of the post and the magnetic structure of the impeller, resulting in reduced axial magnetic forces being generated between the post and the impeller. In particular, the ratio between magnetic torque and axial magnetic force can be increased by reducing the axial magnetic force, said ratio being an important figure in the development of magnetically driven intravascular blood pumps. Said ratio is important because the magnetic flux that can be generated is generally limited, so that it is desirable to use as much as possible of it for torque generation. The technical effect of the concavity is a reduced axial force acting on the rotor in axial direction without losing motor power or, alternatively, an increase of motor power at the same total magnetic flux.

This ratio can be increased even further according to a preferred aspect of the invention by a downward inclination of the front surface within the concavity in a radially outer direction (in addition to being inclined downwardly towards a central area thereof). Thus, relative to the axis of rotation, a radial inner region of the front surface in the concavity protrudes axially beyond a radial outer region of the front surface in the concavity. Again, the result thereof is that the maximum depth of the concavity is increased. As mentioned, the deeper the concavity is, the greater the distance is between the respective portion of the front surface of the post and the magnetic structure of the impeller, resulting in reduced axial magnetic forces being generated between the post and the impeller. Thus, the ratio between the magnetic torque and axial magnetic force can be further increased by the downward inclination of the front surface within the concavity in a radially outer direction.

Another important effect achieved by the downward inclination of the front surface in a radially outer direction is that the bundle of concentrated magnetic field lines is directed radially outward and, thus, impinges on the magnetic structure of the impeller also radially outward as compared to a horizontal front surface. This has a positive effect on the achievable magnetic torque. Again, this results in an improved ratio between magnetic torque and axial magnetic force. Thus, the positive effect of the downward inclination of the front surface within the concavity in a radially outer direction on the ratio between the magnetic torque and axial magnetic force is twofold.

According to a preferred embodiment of the invention, the combination of an inclination of the front surface in the concavity in both directions, centrally and radially outward, leads to a concavity which is open towards a side surface of the post, namely towards a side surface that is located radially outward relative to the axis of rotation. Preferably, the posts have a triangular cross section with three side surfaces, wherein one of the three side surfaces is located radially outward relative to the axis of rotation in comparison to the other two side surfaces. In such a case, the concavity is open towards the one of the three side surface that is located on the radially outer side of the post.

In all of the aforementioned variations, the concavity may preferably have a maximum depth of between 0.05 mm and 0.3 mm.

According to another aspect of the invention, the post does not extend with its impeller-side end radially beyond the impeller-side end of the respective coil winding disposed around the post, wherein the term "radially" relates to a direction transverse, preferably perpendicular, to the longitudinal axis of the respective post. In other words, the posts do not have a particular head portion. Instead, the posts preferably have a constant cross section at least at their impeller-side end region, more preferably along their entire length.

An advantage of posts having no head portion is that magnetic losses due to parasitic flux between neighboring posts are reduced by a greater distance between the posts. The result is again that the ratio between the achievable magnetic torque and the magnetic axial forces between the drive unit and the impeller is increased as compared to the pump described in WO 2017/162619 A1 where the posts extend with their impeller-side ends radially beyond the impeller-side end of the respective coil winding.

According to a further aspect of the invention, the posts may each comprise a soft magnetic material which is discontinuous in cross section transverse, preferably perpendicular, to a longitudinal axis of the respective post, said axis preferably being parallel to the axis of rotation, as is described in further detail in WO 2019/057636 A1. "Discontinuous" in the sense of the present invention means that the soft magnetic material as seen in any cross section transverse to the longitudinal axis is interrupted, separated, intersected or the like by means of insulating material or other materials or gaps in order to form strictly separated areas of soft magnetic material or areas that are interrupted but connected at a different location. In other words, the soft magnetic material of the posts is discontinuous in cross section transverse, preferably perpendicular, to a direction of magnetic flux caused by the respective coil winding in the post. Providing a discontinuous soft magnetic material in cross-sectional planes transverse to the direction of the magnetic flux reduces eddy currents. This further increases the effectiveness of the intravascular blood pump.

Preferably, at least one weld is provided at a surface (811) of the discontinuous soft magnetic material, the weld bridging at least one discontinuity regarding electrical conductivity in the discontinuous soft magnetic material. The weld enables the easy manufacture of a magnetic core or a part of it out of a discontinuous soft magnetic material. That is, when separating the magnetic core or the posts for the magnetic core out of a larger work piece of discontinuous soft magnetic material, the discontinuous soft magnetic material may delaminate or otherwise lose its integrity due to the machining forces which are applied to the work piece during the separating process. This is particularly critical due to the very little dimensions of the magnetic core and especially the posts thereof and may even occur when electrical discharge machining, especially electrical discharge machining by wire cutting, is used for separating the magnetic core, or the posts therefor, out of the work piece. By means of the welds, which are applied to the work piece prior to the separation step, the mechanical stability of the discontinuous material is improved. In the case that electrical discharge machining is used for cutting the magnetic core or posts out of the work piece, also the flow of electric current to the location of cutting is improved. The weld or welds may later form a part of the magnetic core or posts. In particular, an impeller-side end surface of the posts being oriented transverse to the axis of rotation exposes the discontinuous material. Accordingly, the weld or welds may be arranged on the impeller-side surface of the posts.

The drive unit may comprise a back plate connecting the rear ends of the posts. Like the posts, the back plate may comprise a discontinuous soft magnetic material. Since the magnetic flux in the back plate is substantially transverse or perpendicular to the axis of rotation, the soft magnetic material of the back plate may be made discontinuous in cross section parallel to the axis of rotation. Alternatively, the posts and the back plate may be made from a monoblock of discontinuous soft magnetic material such that the soft magnetic material of the back plate and the discontinuous soft magnetic material of the posts is discontinuous in the same direction, preferably discontinuous in cross section perpendicular to the axis of rotation. Apart from that, substantially all features and explanations mentioned above with respect to the discontinuous material of the posts are valid also for the back plate. However, the back plate may alternatively be formed of continuous, i.e. solid, soft magnetic material.

According to one preferred embodiment of a drive unit comprising a back plate which connects the rear ends of the posts, a material of at least one of the posts is integral with a material of an intermediate area of the back plate, wherein the intermediate area of the back plate is an area of the back plate situated between the posts. Preferably, all posts are connected integrally to the back plate in this way. In other words, at least one post and the back plate, preferably the entire magnetic core of the drive unit, can be made of a single block of material, which may also be referred to as a monoblock. An advantage of such a magnetic core is that magnetic resistance at the transition between the posts and the back plate is minimized and, thus, magnetic flux is improved. Further, a good mechanical rigidity of the transition between the posts and the back plate can be achieved.

According to another preferred embodiment of a drive unit comprising a back plate which connects the rear ends of the posts, at least one of the posts and preferably all of the posts contact the back plate with a rear end surface of the respective post. This provides the advantage that the quality of the magnetic connection between the posts and the back plate can be made independent of the quality of the mechanical fastening of the posts to the back plate. For instance, the posts may be mechanically fastened to the back plate in corresponding recesses in the back plate or by means of glue provided around the rear ends of the posts. Thus, a good magnetic connection and, thus, a good magnetic flux can be achieved directly via the rear end surfaces of the posts into the back plate without being forced to accept constraints regarding the mechanical properties of the mechanical connection between the posts and the back plate. Furthermore, a magnetic path for transmission of magnetic flux is established which may exist additionally to a circumferential transmission of magnetic flux in the case where the rear ends of the posts are received in appropriately sized recesses in the back plate.

Thus, in this case the posts may be magnetically connected to the back plate at a corresponding contact plane of the back plate. The contact plane is preferably arranged parallel to the rear end surfaces of the posts. Preferably, it is arranged perpendicular to the axis of rotation. Preferably, the full surface area of the rear end surfaces of the posts is in contact with the back plate. This significantly reduces the magnetic resistance of the connection between the posts and the back plate. An unevenness of the rear end surface and the contact plane of the back plate is preferably such that a resulting gap is not more than 10 μm.

The back plate, like the posts, is preferably made of a soft magnetic material, such as electrical steel (magnetic steel) or other material suitable for closing the magnetic flux circuit, preferably cobalt steel. The diameter of the back plate may be in the range of 3 mm to 9 mm, such as 5 mm or 6 mm to 7 mm. The thickness of the back plate may be in the range of 0.5 mm to 2.5 mm, such as 1.5 mm. The outer diameter of the blood pump may be in the range of 4 mm to 10 mm, preferably 7 mm. The outer diameter of the arrangement of the plurality of posts may be in the range of 3 mm to 8 mm, such as 4 mm to 7.5 mm, preferably 6.5 mm.

As stated above, the posts are made of a soft magnetic material such as electrical steel (magnetic steel). The posts and the back plate may be made of the same material. Preferably, the magnetic core of the drive unit, including the posts and the back plate, is made of cobalt steel. The use of the cobalt steel contributes to reducing the pump size, in particular the diameter. With the highest magnetic permeability and highest magnetic saturation flux density among all magnetic steels, cobalt steel produces the most magnetic flux for the same amount of material used.

The dimensions of the posts, in particular length and cross-sectional area, may vary and depend on various factors. In contrast to the dimensions of the blood pump, e.g. the outer diameter, which depend on the application of the blood pump, the dimensions of the posts are determined by electromagnetic properties, which are adjusted to achieve a desired performance of the drive unit. One of the factors is the flux density to be achieved through the smallest cross-sectional area of the posts. The smaller the cross-sectional area, the higher the necessary current is to achieve the desired magnetic flux. A higher current, however, generates more heat in the wire of the coil due to electrical resistance. Even more importantly, the stator material quickly saturates magnetically if the cross section of the posts is too small. That means, although "thin" posts are preferred to reduce the overall size, this would require high current and, thus, result in undesired heat. The heat generated in the wire also depends on the length and diameter of the wire used for the coil windings. A short wire length and a large wire diameter are preferred in order to minimize the winding loss (referred to as "copper loss" or "copper power loss" if copper wires are used, which is usually the case). In other words, if the wire diameter is small, more heat is generated compared to a thicker wire at the same current, a preferred wire diameter being e.g. 0.05 mm to 0.2 mm, such as 0.1 mm. Further factors influencing the post dimensions and the performance of the drive unit are the number of windings of the coil and the outer diameter of the windings, i.e. the post including the windings. A large number of windings may be arranged in more than one layer around each post, for instance, two or three layers may be provided. However, the higher the number of layers, the more heat will be generated due to the increased length of the wire in the outer layers having a larger winding diameter. The increased length of the wire may generate more heat due to the higher resistance of a long wire compared to a shorter one. Thus, a single layer of windings with a small winding diameter would be preferred, but due to the required power, more than one winding is usually provided.

A typical number of windings, which in turn depends on the length of the post, may be about 50 to about 150, e.g. 56 or 132. Independent of the number of windings, the coil windings are made of an electrically conductive material, in particular metal, such as copper or silver. Silver may be preferred to copper because silver has an electrical resistance which is about 5% less than the electrical resistance of copper.

Preferably, at least one post, more preferably each post, has a triangular cross section transverse to a longitudinal axis of the post. Preferably, the cross section of the post is triangular over its entire length. Triangular posts can utilize the available space inside a pump housing to a high percentage as such posts can be densely packed around the axis of rotation. Preferably, one side of the triangle faces away from the axis of rotation and is curved. The curvature bends around the axis of rotation. The radius of the curvature preferably corresponds to a radius of an outer diameter defined by the plurality of posts arranged about the axis of rotation. By such curvature, a further augmentation of the use of the space inside a cylindrical pump housing can be achieved.

BRIEF DESCRIPTION OF THE DRAWINGS

The foregoing summary as well as the following detailed description of preferred embodiments will be better understood when read in conjunction with the appended drawings. For the purpose of illustrating the present disclosure, reference is made to the drawings. However, the scope of the disclosure is not limited to the specific embodiments disclosed in the drawings. In the drawings.

DETAILED DESCRIPTION

Figure 1:
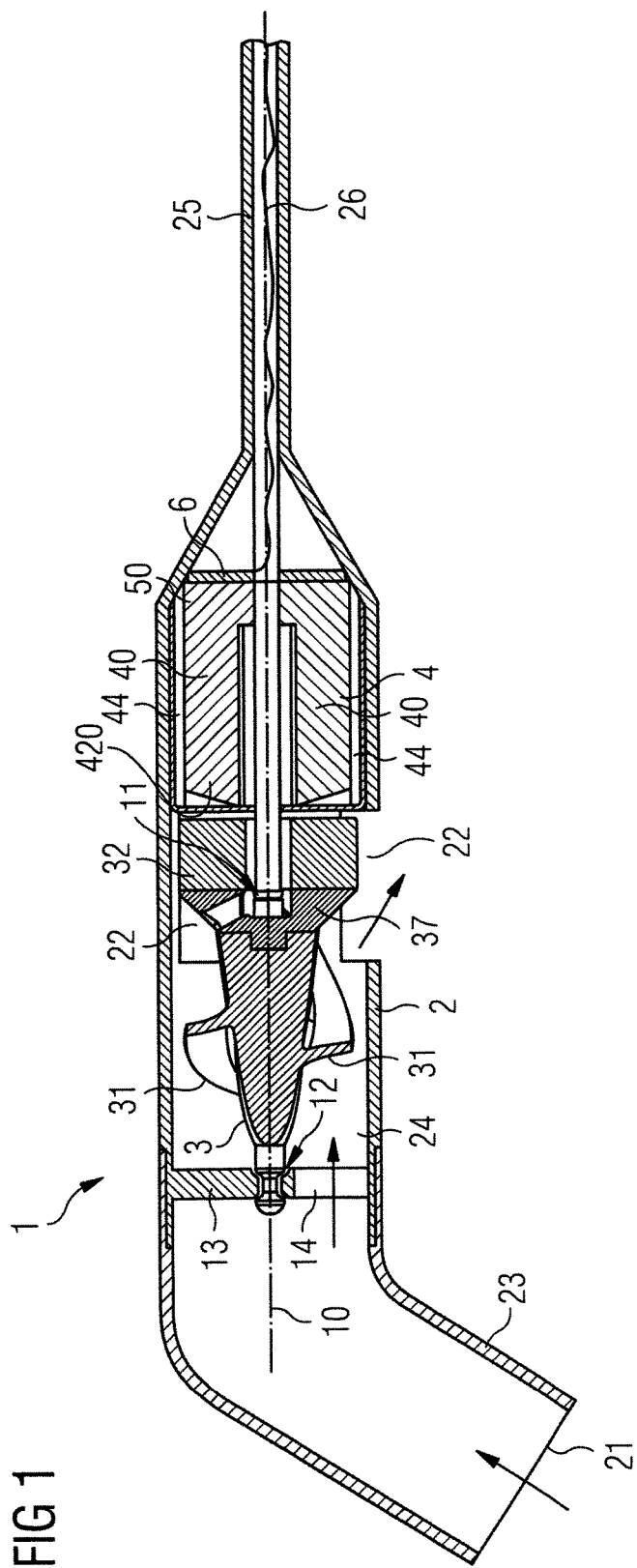
FIG. 1 shows a cross-sectional view of an intravascular blood pump.

Referring to FIG. 1, a cross-sectional view of a blood pump 1 is illustrated. The blood pump 1 comprises a pump casing 2 having a blood flow inlet 21 and a blood flow outlet 22. The blood pump 1 is designed as an intravascular blood pump, also called a catheter pump, and is deployed into a patient's blood vessel by means of a catheter 25. The blood flow inlet 21 is at the end of a flexible cannula 23 which may be placed through a heart valve, such as the aortic valve, during use. The blood flow outlet 22 is located in a side surface of the pump casing 2 and may be placed in a heart vessel, such as the aorta. The blood pump 1 is electrically connected with an electric line 26 extending through the catheter 25 for supplying the blood pump 1 with electric power in order to drive the pump 1 by means of a drive unit 4, as explained in more detail below.

If the blood pump 1 is intended to be used in long-term applications, i.e. in situations in which the blood pump 1 is implanted into the patient for several weeks or even months, electric power is preferably supplied by means of a battery. This allows a patient to be mobile because the patient is not connected to a base station by means of cables. The battery can be carried by the patient and may supply electric energy to the blood pump 1, e.g. wirelessly.

The blood is conveyed along a passage 24 connecting the blood flow inlet 21 and the blood flow outlet 22 (blood flow indicated by arrows). An impeller 3 is provided for conveying blood along the passage 24 and is mounted to be rotatable about an axis of rotation 10 within the pump casing 2 by means of a first bearing 11 and a second bearing 12. The axis of rotation 10 is preferably the longitudinal axis of the impeller 3. Both bearings 11, 12 are contact-type bearings in this embodiment. At least one of the bearings 11, 12 could, however, be a non-contact-type bearing such as a magnetic or hydrodynamic bearing. The first bearing 11 is a pivot bearing having spherical bearing surfaces that allow for rotational movement as well as pivoting movement to some degree. A pin 15 is provided, forming one of the bearing surfaces. The second bearing 12 is disposed in a supporting member 13 to stabilize the rotation of the impeller 3, the supporting member 13 having at least one opening 14 for the blood flow. Blades 31 are provided on the impeller 3 for conveying blood once the impeller 3 rotates. Rotation of the impeller 3 is caused by the drive unit 4 which is magnetically coupled to a magnet 32 at an end portion of the impeller 3. The illustrated blood pump 1 is a mixed-type blood pump, with the major direction of flow being axial. It will be appreciated that the blood pump 1 could also be a purely axial blood pump, depending on the arrangement of the impeller 3, in particular the blades 31.

The blood pump 1 comprises the impeller 3 and the drive unit 4. The drive unit 4 comprises a plurality of posts 40, such as six posts 40, only two of which are visible in the cross-sectional view of FIG. 1. The posts 40 are arranged parallel to the axis of rotation 10, more specifically, a longitudinal axis of each of the posts 40 is parallel to the axis of rotation 10. One end 420 of the posts 40 is disposed adjacent to the impeller. Coil windings 44 are arranged about the posts 40. The coil windings 44 are sequentially controlled by a control to create a rotating magnetic field. A part of the control unit is the printed circuit board 6 which is connected to the electric line 26. The impeller has a magnet 32, which is formed as a multiple-piece magnet in this embodiment. The magnet 32 is disposed at the end of the impeller 3 facing the drive unit 4. The magnet 32 is arranged to interact with the rotating magnetic field so as to cause rotation of the impeller 3 about the axis of rotation 10.

In order to close the magnetic flux path, a back plate 50 is located at the end of the posts 40 opposite the impeller-side of the posts. The posts 40 act as a magnetic core and are made of a suitable material, in particular a soft magnetic material, such as steel or a suitable alloy, in particular cobalt steel. Likewise, the back plate 50 is made of a suitable soft magnetic material, such as cobalt steel. The back plate 50 enhances the magnetic flux, which allows for reduction of the overall diameter of the blood pump 1, which is important for intravascular blood pumps. For the same purpose, a yoke 37, i.e. an additional impeller back plate, is provided in the impeller 3 at a side of the magnet 32 facing away from the drive unit 4. The yoke 37 in this embodiment has a conical shape in order to guide the blood flow along the impeller 3. The yoke 37 may be made of cobalt steel, too. One or more wash-out channels that extend towards the central bearing 11 may be formed in the yoke 37 or the magnet 32.

Figure 2:
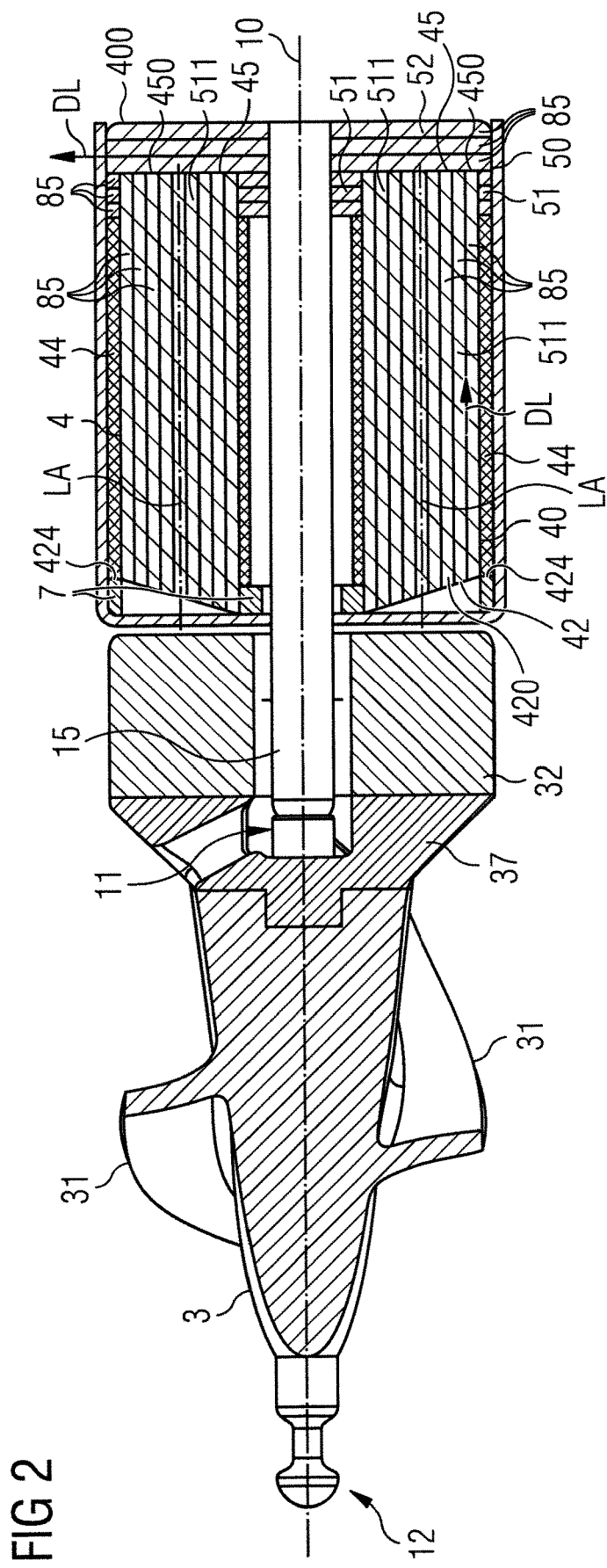
FIG. 2 shows a cross-sectional view of a first embodiment of a drive unit-impeller arrangement.

FIG. 2 shows a cross-sectional view of a first preferred embodiment of a drive unit-impeller arrangement for the blood pump according to FIG. 1. As can be seen in FIG. 2, the impeller-side ends 420 of the posts 40 do not extend radially beyond the windings 44. Rather, the cross section of the posts 40 is constant in the direction of a longitudinal axis LA of the posts 40. It is thus avoided that the posts 40 come close to each other, as this could cause a partial magnetic short-circuit with the result of a reduced power of the electric motor of the blood pump.

The drive unit according to FIG. 2 may comprise at least two posts 40. The number of posts is preferably a multiple of three and, thus, may be three, nine or twelve. Alternatively, the number of posts 40 may be a multiple of two, such as two, four, six, eight, ten or twelve. Higher numbers of posts 40 may be possible. A number of six posts 40 is preferred. Due to the cross-sectional view, only two posts 40 are visible. The posts 40 and the back plate 50 form a magnetic core 400 of the drive unit 4 which may have a diameter of less than 10 mm.

The posts 40 may, as shown, consist of a discontinuous soft magnetic material that is discontinuous in regard of electrical conductivity. The discontinuous soft magnetic material comprises a plurality of sheets 85 which are made of a ferromagnetic material and which are laminated to each other. A direction of lamination is arranged in direction of the longitudinal axis LA of the posts 40 and marked by an arrow DL. As shown, the posts 40 are arranged in parallel to the axis of rotation 10.

A spacer 7 is disposed around the posts 40. It is made of a magnetically inactive material and has the purpose of keeping the distance of the posts 40 constant at their impeller-side ends 420. The spacer 7 will be described in further detail in regard to FIGS. 6A to 6C. The impeller-side ends 424 of the coil windings 44 extend up to the spacer 7. At the other ends of the posts 40, the back plate 50 is provided. According to the embodiment shown in FIG. 2, the back plate 50 has recesses for receiving therein the posts 40. More specifically, it comprises a first layer 51 with openings 511 for rear ends 450 of the posts 40. The back plate 50 will be described in further detail in regard to FIGS. 7A to 7C.

It is conceivable to realize embodiments of the blood pump 1 with arbitrary combinations of the three above-mentioned features: no radial extension of the impeller-side ends 424 of the posts beyond the impeller-side ends of the windings 44, provision of a magnetically inactive spacer 7 between the posts 40, and back plate 50 with recesses for receiving the rear ends 450 of the posts 40.

Figure 3A:
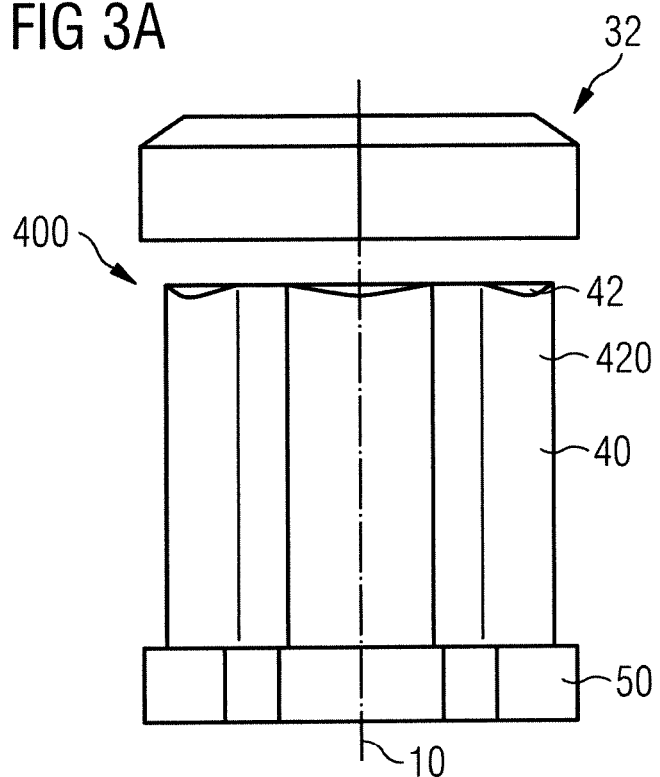
FIGS. 3A and 3B show a side view and a perspective view of the magnetic core of the drive unit of the drive unit-impeller arrangement according to FIGS. 1 and 2.
Figure 3B:
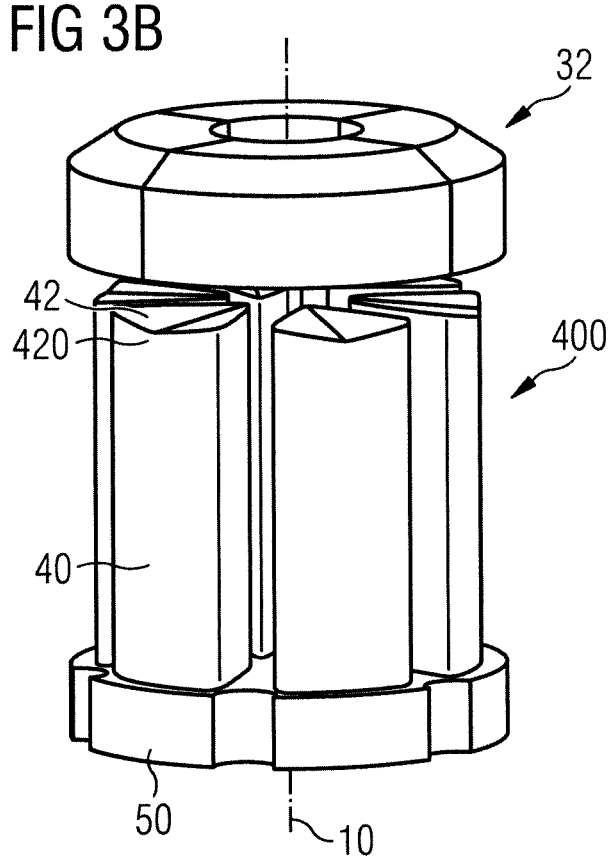

FIGS. 3A and 3B show a side view and a perspective view of the magnetic core 400 of the drive unit 4 of the drive unit-impeller arrangement according to FIGS. 1 and 2. The posts 40 and back plate 50 of the magnetic core 400 are shown with a distance to the magnetic structure 32 of the impeller 3. As can be seen, the front surface 42 of each of the impeller-side ends 420 of the posts 40 is provided with a concavity. In this particular embodiment and in all embodiments described hereinafter, the concavity extends over the entire front surface 42 such that the circumference of the concavity coincides with the circumference of the front surface 42.

Thus, the inclination of the concavity extends up to the circumference of the front surface 42. The concavity has a triangular cross section when viewed in a cross-sectional plane running vertically through the front surface 42, said plane, in the embodiment shown, being perpendicular to the longitudinal axis of the respective post 40. This would be different in embodiments in which each of the front surfaces 42 of the posts 40 is inclined so as to form together a cone-shaped front side of the magnetic core 400, as described in WO2017/162619 A1. That is, in WO2017/162619 A1, the posts each have a shaft and an inclined head portion at the impeller-side end of the shaft. Also, the front surface of those head portions, albeit inclined, may be provided with the afore-described concavity in which the front surface is inclined downwards towards a central area of the front surface and has a triangular cross section when viewed in a cross-sectional plane running vertically through the front surface.

The inclination of the front surface 42 within the concavity downwards towards a central area of the front surface serves to concentrate and, thus, bundle the magnetic field lines running through the front surface, as will be explained further below in relation to FIG. 4. However, inside the concavity the front surface 42 is not only inclined downward towards the central area of the front surface 42 but is further inclined downwards in a radially outer direction relative to the axis of rotation 10. In other words, the radial inner region of the front surface 42 in the concavity protrudes axially beyond a radial outer region of the front surface 42 in the concavity. The purpose of the downward inclination radially outwards has the purpose of directing the magnetic field lines towards the outer periphery of the magnetic structure 32 of the impeller, thereby increasing the lever arm by which the impeller 3 is rotated and, thus, increasing the torque. Consequently, the inclination of the concavity both towards the center of the front surface 42 as well as radially outwards results for a post 40 with a triangular cross section in that the concavity is open towards the side surface of the post 40 which is located radially outwards relative to the axis of rotation. The point of maximum depth of the front surface 42 is, thus, positioned at the outer circumference of the respective post 40 and may range between 0.05 mm and 0.3 mm, preferably between 0.1 mm and 0.2 mm, and is most preferably about 0.2 mm.

Figure 4:
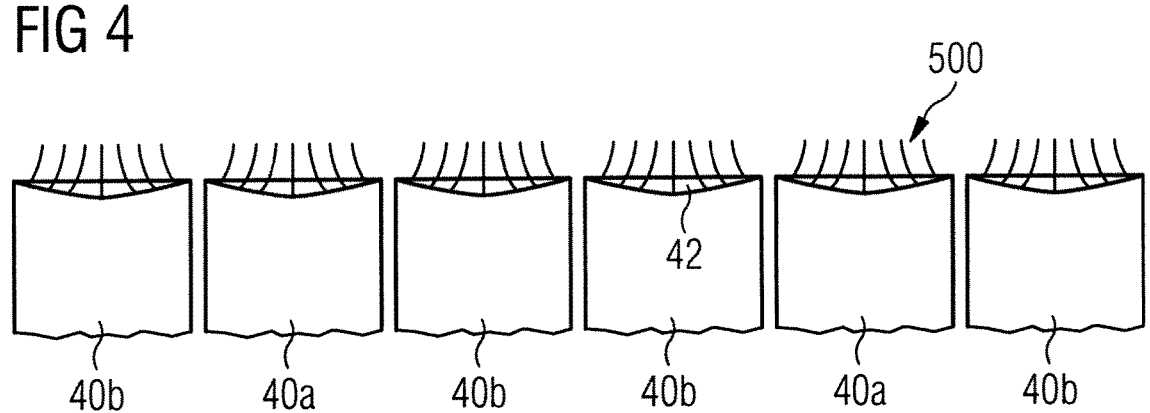
FIG. 4 shows schematically a winding off of the six posts of the magnetic core shown in FIGS. 3A and 3B.

FIG. 4 shows schematically a winding off of six posts 40a, 40b of a magnetic core 400, such as the magnetic core 400 shown in FIGS. 3A and 3B. In order to create a rotating magnetic field, two aspects are important. First, some of the posts must be magnetized in a positive direction while the others are magnetized in a negative direction so that the magnetic fluid lines of the magnetic flux extend from the positive by magnetized posts through the magnetic structure of the impeller 32 into the negatively magnetized posts and further through the back plate 50 back into the positively magnetized posts so as to create a closed magnetic field. Second, the direction of magnetization of the posts must be sequentially changed from post to post in a circumferential direction so as to drag the magnetic structure 32 of the impeller 3 rotationally about the axis of rotation 10. In order to achieve this, neighboring posts are magnetized in opposite directions by an appropriately directed current running through the coil windings 44 provided around each of the posts 40. For instance, a first post may be magnetized positively, a second, neighboring post negatively, a third, neighboring post positively, a fourth, neighboring post again negatively, and so forth. In a preferred embodiment, however, there are always two neighboring posts magnetized in one direction to drag the magnetic structure 32 of the impeller 3, and only one of the next following posts is magnetized oppositely. In the case of six posts, four posts 40b are magnetized in one direction and two posts 40a are magnetized in the opposite direction, as indicated in FIG. 4 in which a winding off of the six posts is schematically displayed. As can further be seen from FIG. 4, the magnetic field lines 500 extending through the concave front surface 42 are concentrated due to the inclined surfaces in the concavity so that the magnetic field lines form a bundle. The danger of a short circuit in the sense that magnetic field lines 500 bridge between neighboring posts 40a and 40b is, thus, minimized.

FIGS. 5A to 5D each show a side view on the impeller-side end 420 of a post according to four different embodiments. The embodiment shown in FIG. 5A corresponds to the previously described embodiment with a concavity having a circumference which coincides with the circumference of the front surface 42 and having two inclined side walls 42a which are inclined both downwards towards the central area of the front surface 42 and radially outwards relative to the axis of rotation, as explained above. As a result, the concavity has a triangular cross section when viewed in any cross-sectional plane running vertically through the front surface 42, and is open on the radially outer side of the post.

Figure 5A:
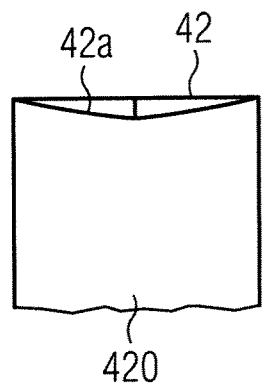
FIGS. 5A to 5D each show a side view on the impeller-side end of a post according to four different embodiments.
Figure 5B:
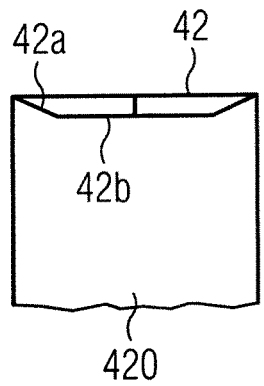

The embodiment shown in FIG. 5B substantially corresponds to the embodiment of FIG. 5A except that it has a flat bottom 42b. Thus, the triangular cross section of the concavity is limited to the radially inner side of the post relative to the axis of rotation. Further radially outwards, the cross section is trapezoidal. Thus, the bottom 42b is flat and parallel to the general plane of the front surface 42, whereas the side walls 42a are straight-lined side walls with oppositely oriented inclinations.

Figure 5C:
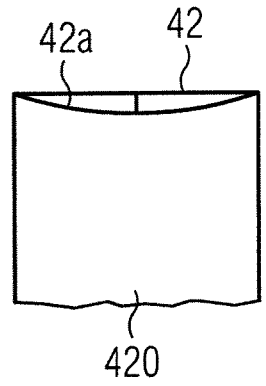

In the embodiment shown in FIG. 5C, the concavity has a curved inclined side wall 42a so that the inclination of the concavity is maximal at the circumference of the front surface 42.

Figure 5D:
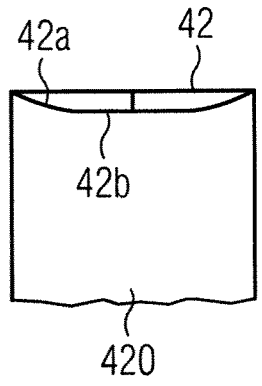

The embodiment shown in FIG. 5D is a combination of the embodiment shown in FIGS. 5B and 5C. That is, the concavity has a flat bottom 42b and curved inclined side walls 42a.

Figure 6A:
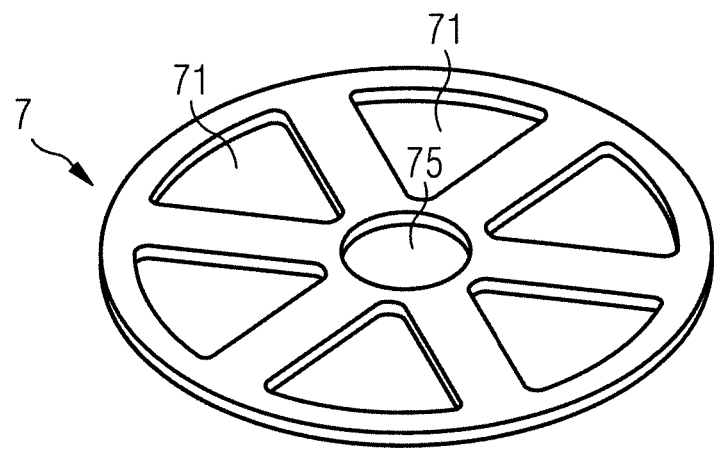
FIG. 6A shows a spacer for the drive unit-impeller arrangement according to FIG. 2 in a perspective view.
Figure 6B:
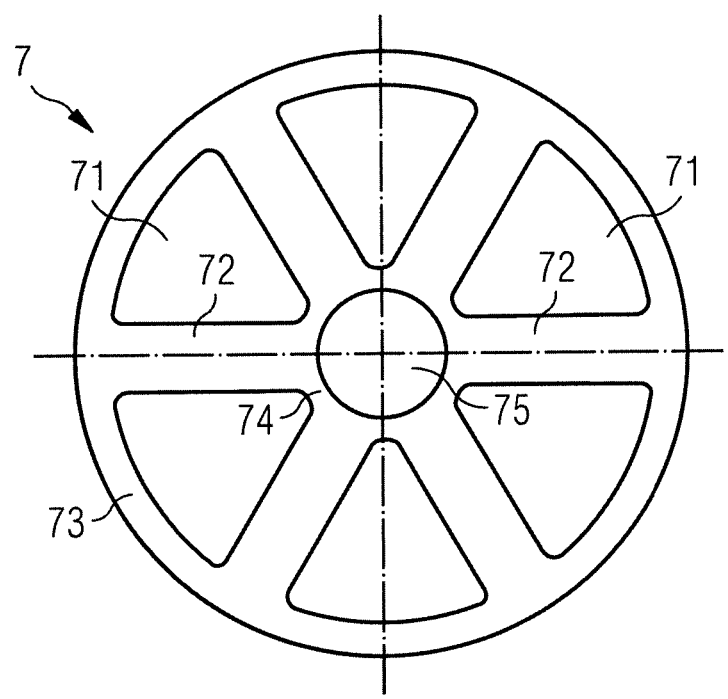
FIG. 6B shows a front view of the spacer of FIG. 3A.
Figure 6C:
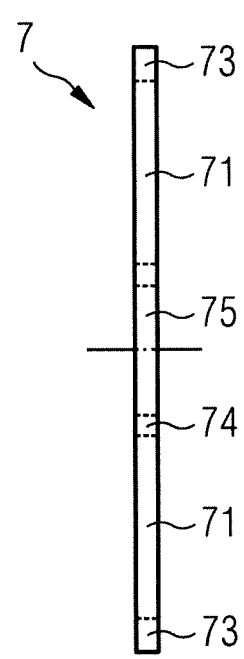
FIG. 6C shows a side view of the spacer of FIGS. 3A and 3B.

FIGS. 6A to 6C show a perspective view, a front view and a side view of the spacer 7, respectively. The spacer 7 generally has the form of a disk or a wheel with a through hole 75 in the middle. The spacer 7 comprises an opening 71 for each of the posts. For an embodiment with six posts 40, six openings 71 are present as shown. Between the openings 71, distancing spokes 72 are arranged. When the posts 40 are inserted in the openings 71, the distancing spokes 72 keep the distance between the posts 40 constant. Further, the spacer 7 comprises an outer rim 73 and an inner rim 74 which connect neighboring distancing spokes 72 and which stabilize the spacer. The spacer 7 is made of titanium which is a paramagnetic material that avoids a magnetic short circuit when arranged between the impeller-side ends 420 of the posts 40. Titanium provides a high mechanical strength such that it allows manufacturing of the spacer 7 with little thickness. This is advantageous regarding consumption of construction space. Also, titanium has low electrical conductivity so that eddy current losses are minimal, and titanium is easy to machine. However, any other non-magnetic material may likewise be used, provided it is stable, machinable with high precision and does not easily conduct electricity. The use of diamagnetic material is also possible, as it counters the outer magnetic field.

Figure 7A:
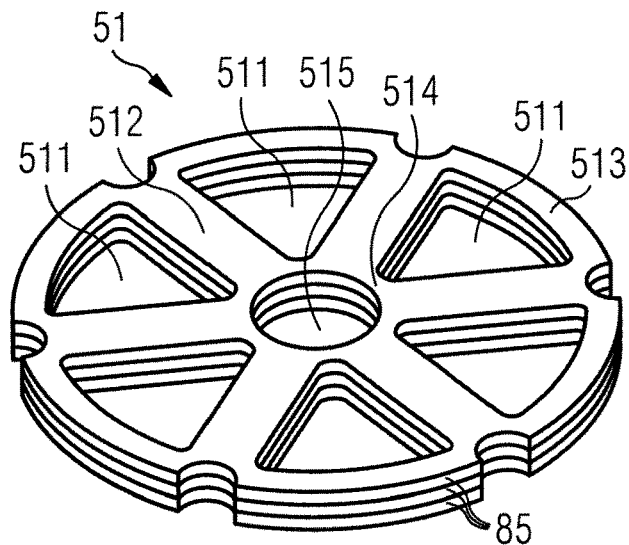
FIG. 7A shows a perspective view of a first layer of a back plate with openings for posts of the drive unit of the arrangement according to FIG. 2.

FIG. 7A shows the perspective view on a first layer 51 of the back plate 50. The first layer 51 has a general shape of a disk or a wheel with a central hole 515. The first layer 52 comprises openings 511 into which the rear ends 450 of the posts 40 will be arranged. The first layer 51 comprises distancing spokes 512 between the openings 511. One purpose of the distancing spokes 512 is to keep the distance between the rear ends 450 of the posts 40 constant. Further, the first layer 51 comprises an outer rim 513 and an inner rim 514 which connect the distancing spokes 512 at the outer radial end and the inner radial end of the openings 511, respectively. The first layer 51 may be made of a discontinuous soft magnetic material which is discontinuous in regard to electrical conductivity. It may comprise several ferromagnetic sheets 85, particularly three sheets, as shown in FIG. 7A. The sheets 85 are laminated together with an electrically non-conductive material to form the discontinuous soft magnetic material. A direction of lamination DL is generally parallel to the sheets 85, and the direction of the main extension of the sheets defines the plane of lamination. Within the back plate 50, the sheets 85 are perpendicular to the axis of rotation 10. In the center of the first layer 51, a hole 515 is arranged. It has the purpose of easing the assembly of the first layer 51 and the second layer 52, e.g. it may serve to center the first and second layers 51, 52.

Figure 7B:
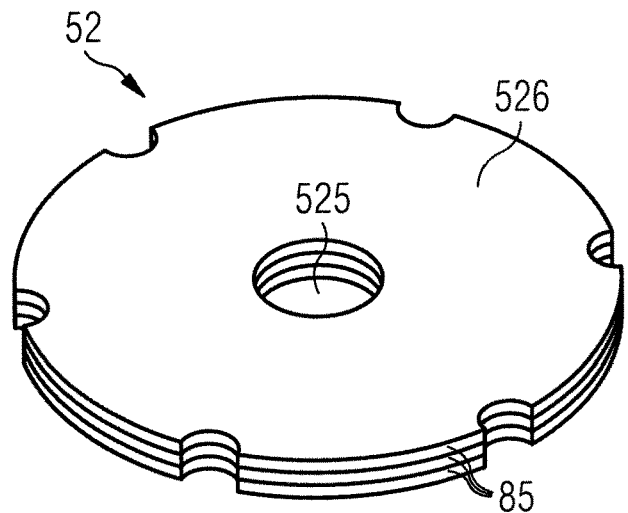
FIG. 7B shows a perspective view of a second layer of the back plate without openings for posts of the drive unit of the arrangement of FIG. 2.

In FIG. 7B, a perspective view of a second layer 52 of the back plate 50 is shown. The second layer 52 has substantially the form of a disk with a hole 525 in the center corresponding to the hole 515 in the first layer 51. The second layer 52 does not have any openings for the rear ends of the posts 40. Instead, the second layer 52 provides a contact plane 526 facing the rear ends 450 of the posts 40. The rear ends 450 of the posts, in an assembled state of the drive unit, are in contact with the contact plane 526 of the second layer 52 of the back plate 50 to transmit magnetic flux between the rear ends 450 of the posts 40 and the back plate 50. As all of the rear ends 450 of the posts 40 are in contact with the contact plane 526, magnetic flux can be exchanged between the posts 40, and a magnetic zero point may form in the second layer 52. In order to enable this, the second layer 52 is made of a soft magnetic material. The soft magnetic material may be a discontinuous soft magnetic material which is discontinuous in regard to electrical conductivity and may comprise sheets 85 which are laminated together, similar to the structure as described above in relation to the first layer 51. As an example, three sheets 85 as shown in FIG. 7B may form the second layer 52. In the second layer 52, the direction of lamination D is perpendicular to the axis of rotation 10. The sheets 85 are ferromagnetic and electrically conducting, whereas intermediate layers between the sheets 85, which are not explicitly shown, are non-ferromagnetic and electrically non-conducting. This type of discontinuous soft magnetic material reduces eddy currents which would otherwise be generated to a greater amount by changes of magnetic flux. The hole 525 in the middle of the second layer 52 has the purpose of easing the assembly of the first layer 51 and the second layer 52, e.g. it may serve to center the first and second layers 51, 52.

Figure 7C:
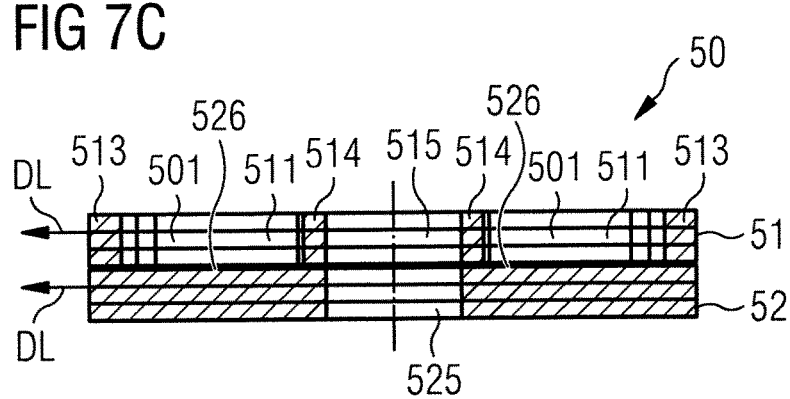
FIG. 7C shows a cross-sectional view of the assembled back plate comprising the first and the second layers of FIGS. 7A and 7B.

FIG. 7C shows a cross section of the back plate 50. It is composed of the first layer 51 and the second layer 52 which are bonded to each other at their main surfaces having the greatest extension. Bonding between the first layer 51 and the second layer 52 of the back plate 50 can be established in the same manner as between the sheets 85 of the first and the second layers 51, 52. The through holes 515 and 525 of the first layer 51 and the second layer 52 are aligned with each other so as to center the first and second layers 51, 52. By stacking the first and second layers 51, 52, the openings 511 are closed at one end by the second layer 52 such that recesses 501 are formed for accommodation of the rear ends 450 of the posts 40. The bottom of the recesses 501 forms the contact plane 526. When a post 40 is inserted into a recess 501, its rear end 450 contacts the contact plane 526. Furthermore, the position of the post 40 is fixed by the distancing spokes 512 as well as by the outer and inner rims 513, 514 which together surround each of the posts 40. In this way, a magnetic connection is established between the second layer 52 and the rear end surfaces 45 of posts 40 at the contact plane 526 and, additionally, a second magnetic connection is established between the posts 40 and the above-mentioned surrounding parts of the first layer 51. However, the main part of the magnetic flux is transferred via the contact plane 526. Preferably, both the surface at the rear end 450 of the posts 40 and the contact plane 526 have a predefined evenness. This way, gaps between the surface 45 at the rear end 450 of the posts 40 and the contact plane 526 may be kept below a certain value of preferably less than 10 μm. This improves the transfer of magnetic flux between the posts 40 and the back plate 50. Preferably, no additional material is present between the surface 45 at the rear end 450 of the posts 40 and the contact plane 526. In this embodiment of the invention, the transfer of magnetic flux via the surface 45 and the back plate 50 is independent of the manner of fastening the posts 40 to the back plate 50.

Figure 8B:
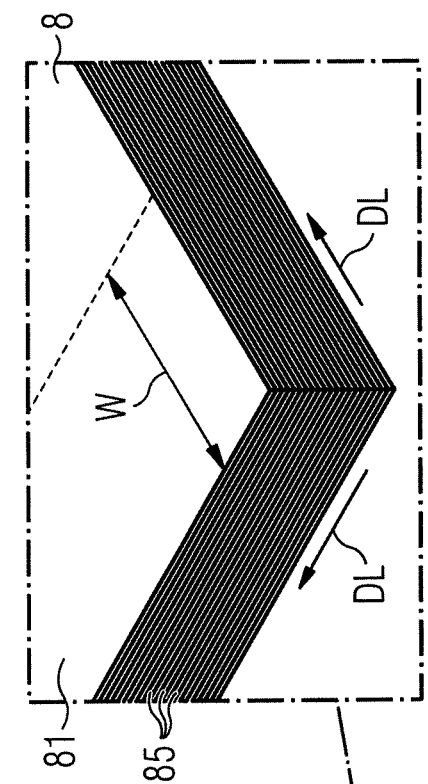
FIGS. 8A to 8D show stages of manufacturing an intermediate product for the further manufacture of posts for the drive unit of the arrangement according to FIG. 2.
Figure 8D:
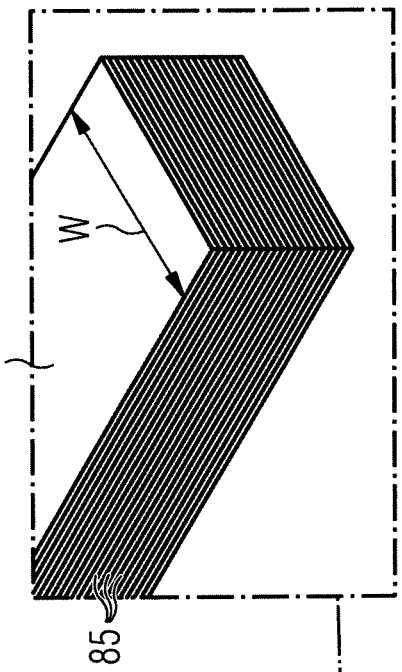
Figure 8A:
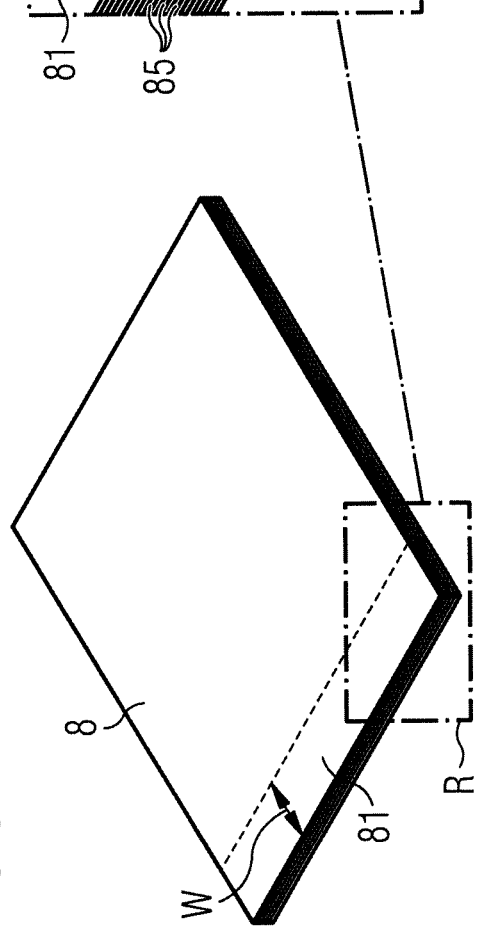

FIGS. 8A to 8D show a preparation step for the production of the posts 40. FIG. 8A shows a perspective view of a plate 8 made of discontinuous soft magnetic material which is discontinuous regarding electrical conductivity, which is hereinafter also referred to as a work piece.

In FIG. 8A, the plate 8 is marked with a width W for cutting a work piece rod 81 off from the plate 8. The width W of the work piece rod 81 is identical to a length of a post 40 to be manufactured from the work piece rod 81. An enlarged view of the portion marked by the rectangle R in FIG. 8A is shown in FIG. 8B. Here, stacked sheets 85 of the discontinuous soft magnetic material are visible. The direction of lamination DL runs along the main plane of the plate 8 and, thus, forms the plane of lamination.

Figure 8C:
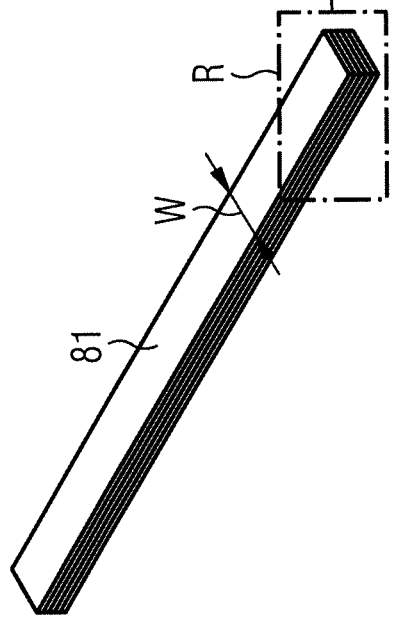

FIG. 8C shows the work piece rod 81 cut-off from the plate 8 as a separate piece of discontinuous material. An enlarged view of the portion marked by the rectangle R in FIG. 8C is shown in FIG. 8D. The sheets 85 of the work piece rod 81 are visible in this view.

Figure 9A:
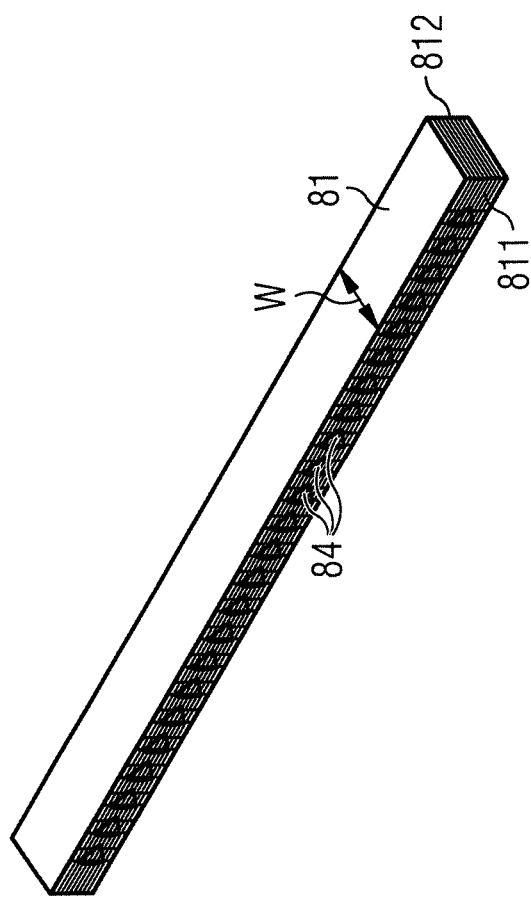
FIGS. 9A to 9C show welds on the intermediate product according to FIG. 5C.

FIG. 9A shows the work piece rod 81 of FIGS. 8C and 8D forming the basis for a welding step in preparation of cutting posts 40 out of the rod 81. On a side plane of the rod 81 pointing to the left side in FIG. 9A, a plurality of cross sections 84 of posts 40 to be manufactured from the rod 81 are depicted. The posts 40 are manufactured by cutting these cross sections 84 out of the rod 81. As the width W of the rod 81 corresponds to the length of the posts 40, the side faces 811 and 812 of the rod 81 become end surfaces at the impeller-side end 420 and the rear end 450 of the posts 40.

Figure 9B:
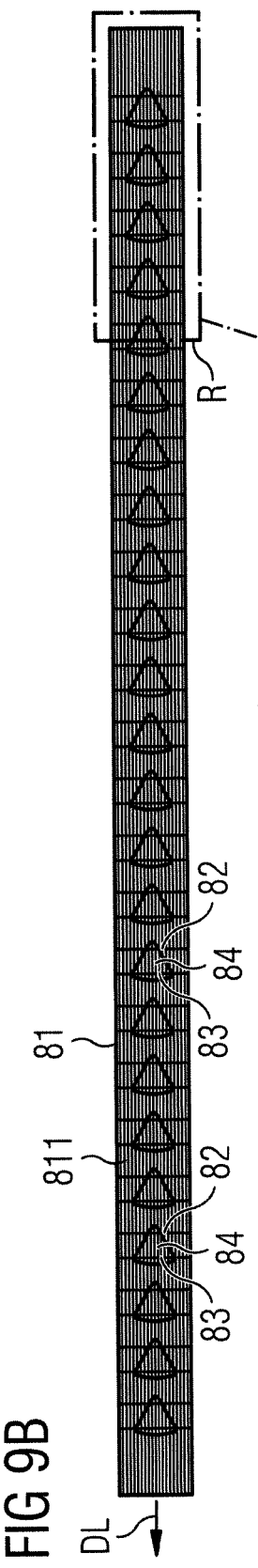

FIG. 9B shows the next preparation step before cutting out the posts 40. Two weld seams 82 and 83 are welded on the face 811 of the rod 81 at a distance to each other and across each of the cross sections 84 of a post 40 to be cut out. The weld seams 82 and 83 run perpendicular to the direction of lamination DL of the sheets 85. In this way, the sheets of the discontinuous material are connected to each other. Instead of two weld seams, a single weld seam may be provided. In addition, similar weld seams may be provided on the opposite side face 812 of the rod 81. The sheets 85 have a better mechanical connection to each other due to the weld seams 82 and 83 and are also electrically connected. The latter has the advantage that electrical current can flow from any position of the discontinuous soft magnetic material which is supposed to become a post 40 to each position of electrical connection of the rod 81, which may be required e.g. for electrical discharge machining. This way, electrical discharge machining is facilitated significantly. Furthermore, higher process reliability is achieved as the cut-out posts 40 cannot delaminate. Preferably, laser welding is applied. It may be advantageous to apply welding power to the same weld twice or even more often. The portion of the rod 81 which is marked by the rectangle R is shown enlarged in FIG. 9C.

Figure 9C:
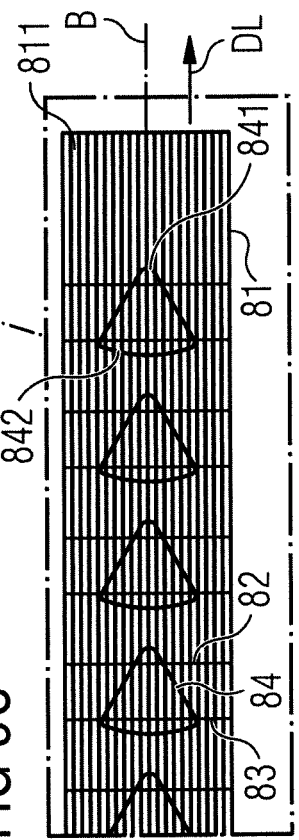

Thus, FIG. 9C shows a plurality of cross sections 84 of posts 40 which are to be cut out of the rod 81. The cross sections 84 have a substantially triangular shape. As shown, the corners may be rounded. A convex side 842 of the triangle which is shown at the left side of the cross section 84 in FIG. 9C has a convex form. This type of cross section 84 is advantageous in order to fully utilize the available construction space inside the cylindrical pump housing 2. A bisector line of a corner 841 of the cross section 84 which is opposite to the convex side 842 of the cross section 84 is aligned with the direction of lamination DL. This way, the sheets 85 run symmetrically through the cross section 84.

Figure 10:
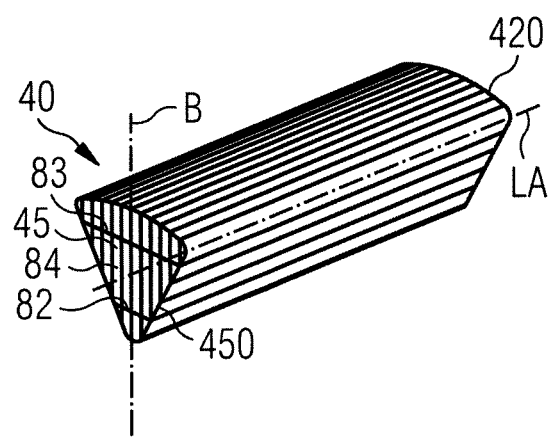
FIG. 10 shows a perspective view of a post which is separated out of the intermediate product as prepared according to FIGS. 8A to 9C.

FIG. 10 shows a post 40 which has been cut out of a rod 81. As can be seen, the weld seams 82 and 83 are still present on the surface 45 at the rear end 450 of the rod 81. The post 40 has a constant cross section 84 along its entire length. If required, the weld seams 82 and 83 may be deburred after cutting out the post 40. At the same time or in a subsequent step, a concavity with a structure as shown in any one of the FIGS. 5A to 5D or with a different structure is cut into the surface at the opposite end of the post 40, said surface will later form the front surface 42 of the impeller-side end 420 of the post 40. Alternatively, the concavity may be formed before providing the welds and cutting out the posts 40 out of the rod 81, such as by wire-electro discharge machining.

Figure 11:
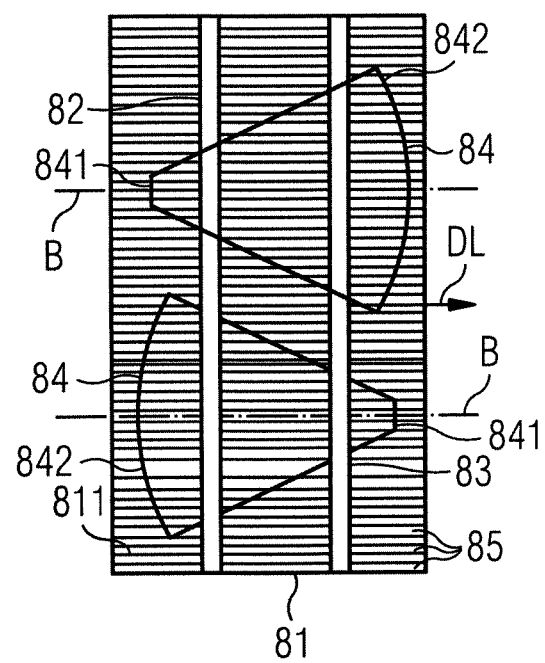
FIG. 11 shows a front view on a plane of the intermediate product of FIG. 9A with two weld seams and two cross sections of posts that are to be cut out of the intermediate product.

FIG. 11 shows another arrangement of two cross sections 84 on a side face 811 of a work piece rod 81. In contrast to the work piece rods 81 shown in FIGS. 9A to 9C, the side surface 811 of the work piece rod 81 of FIG. 11 has a size which allows for disposing two cross sections 84 beside each other in a direction perpendicular to the direction of lamination DL. The cross sections 84 are oriented relative to the direction of lamination DL such that the bisector line B of a corner of each of the cross sections 84 opposite to its respective convex side 842 is aligned with the direction of lamination DL. This way of disposing the cross sections 84 along the rod 81 saves material. Less waste material is produced. It is conceivable to stack even more cross sections 84 of posts 40 in a direction perpendicular to the direction of lamination DL, depending on the thickness of the rod 81 and the required cross-sectional dimensions of the posts 40.

Each of the weld seams 82 and 83 runs across each of the cross sections 84. The weld seams 82, 83 run across the entire side face 811 of the rod 81 in a direction perpendicular to the direction of lamination DL. This way, all sheets 85 of the discontinuous soft magnetic material of the rod 81 are connected with each other.

Figure 12:
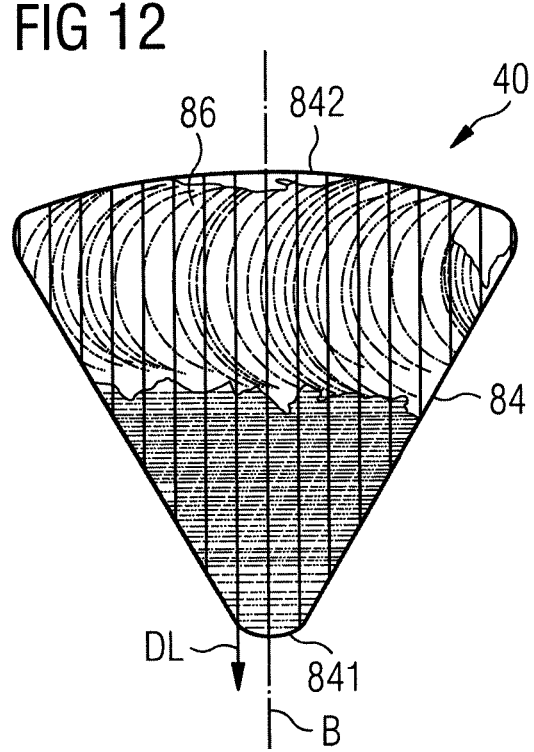
FIG. 12 shows a front view of an end surface of a post with a weld.

FIG. 12 shows an example of a post 40 cut out from a welded rod 81, namely a front view on the rear end surface 45 of the post 40. As shown in FIG. 12, a single weld seam 86 of a considerable width, which may cover more than about one third of the height of the triangular cross section 84, runs along the convex side 842 of the cross section 84. The weld seam 86 runs perpendicular to the direction of lamination DL so as to connect all sheets thereof. However, two weld seams as shown in FIG. 11 are preferred over a single seam. Again, a bisector line B of a corner 841 opposite to the convex side 842 is aligned with the direction of lamination DL.

Figure 13:
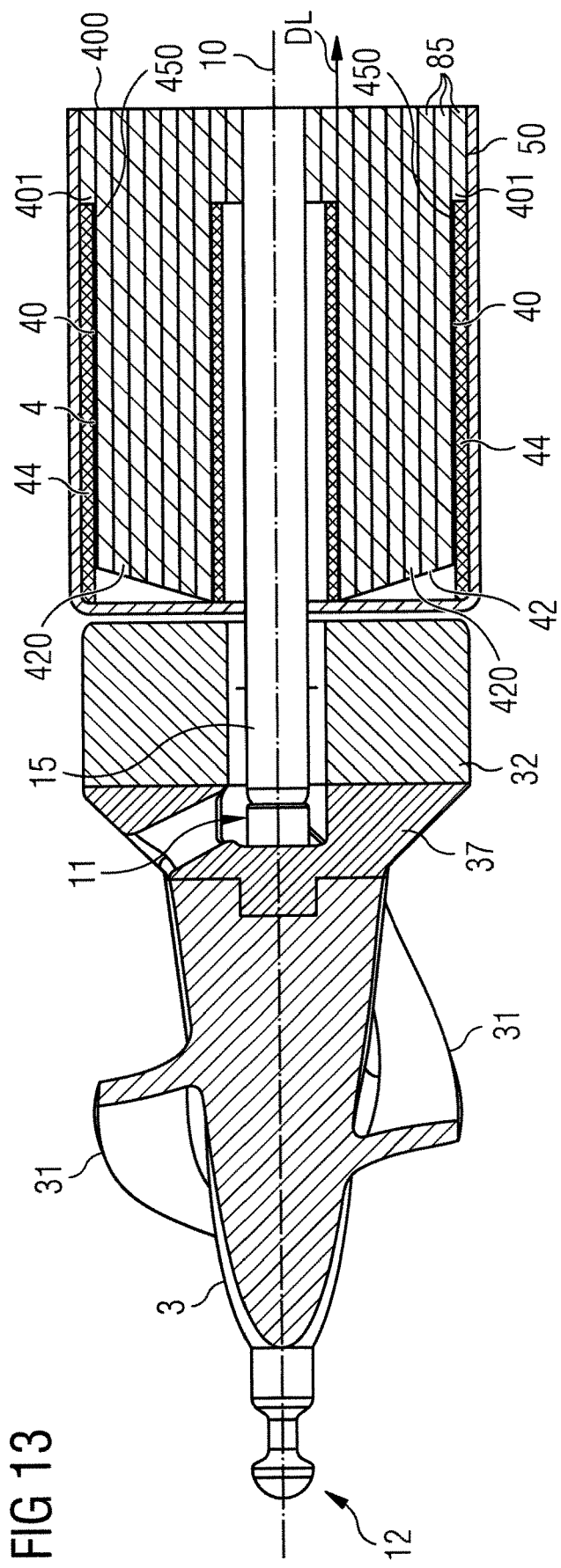
FIG. 13 shows a cross-sectional view of a second embodiment of a drive unit-impeller arrangement.

FIG. 13 shows a second embodiment of a drive unit-impeller arrangement for the blood pump 1 according to FIG. 1. Similar to the first embodiment shown in FIG. 2, the front surface 42 of the impeller-side end 420 has a concavity which tapers away from the magnetic structure 32 of the impeller 3 in a radially outward direction. In addition, the impeller-side ends 420 of the posts 40 do not extend radially beyond the windings 44. Rather, the cross section of the posts 40 is constant in the direction of the longitudinal axis LA of the posts 40. It is thus avoided that the posts 40 come close to each other, as this could cause a partial magnetic short circuit and, thus, reduce the power of the electric motor of the blood pump.

Again, the drive unit according to FIG. 13 may comprise at least two posts 40. The number of posts is preferably a multiple of three and, thus, may be three, nine or twelve. Alternatively, the number of posts may be a multiple of two, such as two, four, six, eight, ten or twelve. Higher numbers of posts 40 may be possible. A number of six posts 40 is preferred. Due to the cross-sectional view, only two posts 40 are visible. The posts 40 and the back plate 50 form a magnetic core 400 of the drive unit 4 which may have a diameter of less than 10 mm.

This second embodiment differs from the first embodiment shown in FIG. 2 by a different structure of the magnetic core. Here, the magnetic core 400 comprises the magnetic components of the drive unit 4, which are the posts 40 and the back plate 50, as one single piece or monoblock. The monoblock consists of discontinuous soft magnetic material. The discontinuous soft magnetic material is discontinuous regarding electrical conductivity. As shown, it comprises a plurality of sheets 85 of ferromagnetic material which are laminated together to form a monoblock 9 as shown in FIG. 14C. The direction of lamination DL is parallel to the axis of rotation 10.

The coil windings 44 extend up to the impeller-side end 420 of the posts 40. This has the advantage that a magnetomotive force can be generated along the entire post 40. The magnetic core 400 comprises a protrusion 401 at the rear end 450 of the posts 40 protruding radially away from the posts 40. This protrusion 401 forms a stop for the coil windings 44 towards the back plate 50. As the integral magnetic core 400 connects the back plate 50 and the posts 40 with high rigidity, a spacer between the posts 40 at the impeller-side end 420 of the posts may be omitted. The integral magnetic core 400 provides the advantage that an optimum magnetic connection between the posts 40 and the back plate 50 is achieved. The magnetic core 400 may have a diameter of less than 10 mm.

Figure 14A:
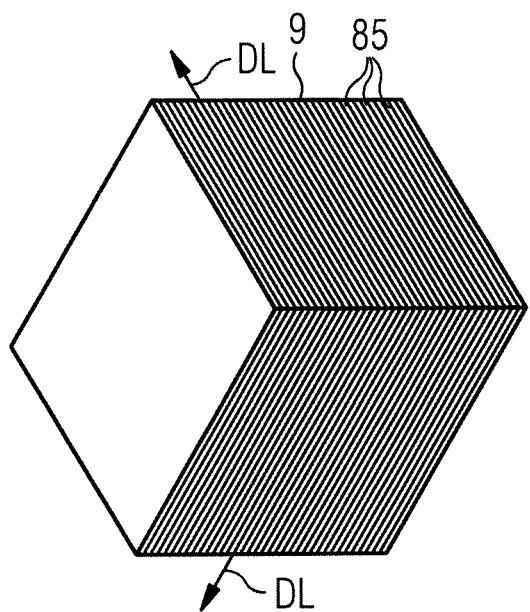
FIGS. 14A to 14C show steps of manufacturing an integrated magnetic core for the drive unit according to FIG. 13.
Figure 14B:
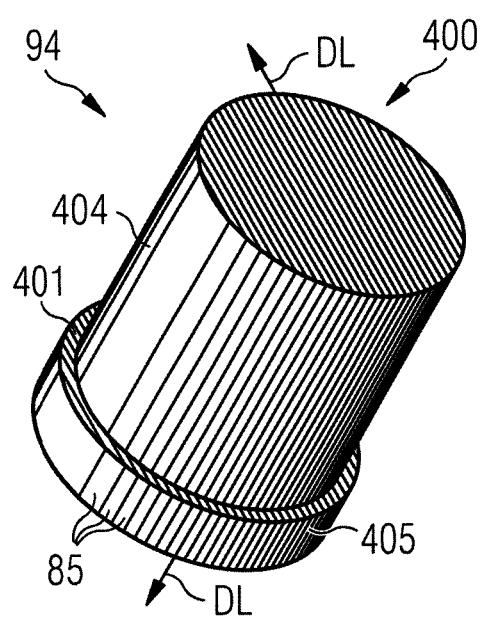
Figure 14C:
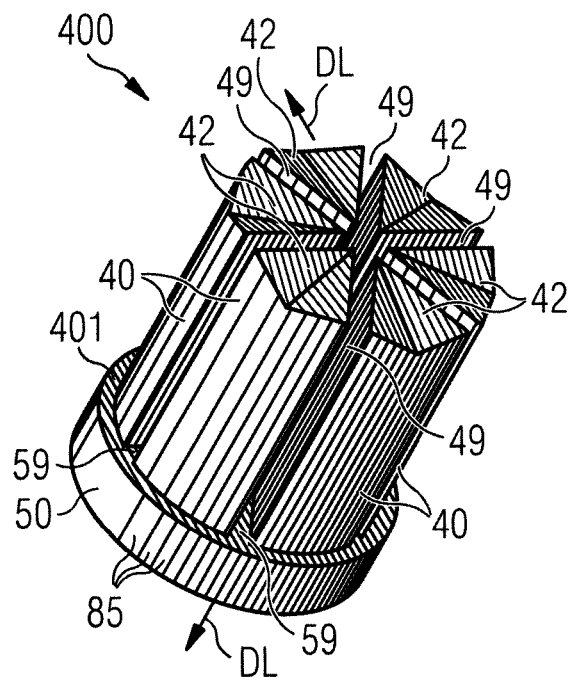

FIGS. 14A to 14C show steps of manufacturing the magnetic core 400 for the drive unit 4 of the drive unit-impeller arrangement as shown in FIG. 13. FIG. 14A shows a perspective view of a monoblock 9 in cubical shape which forms a work piece for manufacturing the magnetic core 400. The monoblock 9 consists of a discontinuous soft magnetic material which is discontinuous regarding electrical conductivity. It comprises sheets 85 which are oriented in a direction of lamination DL which runs along the main plane of the sheets 85. The sheets 85 are each bonded to their respective neighboring sheet by a bonding layer of electrical non-conductive material, which is not explicitly shown in FIGS. 14A to 14C.

FIG. 4B shows the magnetic core 400 in a semi-manufactured state in which it has been machined from the cubical monoblock 9 into a substantially cylindrical body 94. In this machining step, the protrusion 401 is manufactured. A section 404 of reduced diameter of the body 94, which forms a peripheral surface of the posts 40 of the magnetic core 400, is manufactured with a diameter that corresponds to an outer radius of the outermost convex side surfaces 842 of the posts 40.

Then, the body 94 is further manufactured to produce the magnetic core 400 as shown in FIG. 14C. For this production step, electrical discharge machining can be used. For instance, electrical discharge machining by wire cutting can be applied to produce the slots 49 which separate the posts 40 from each other. Inside the slots, space for the coil windings 44 is provided. At the bottom of the slots 49, an intermediate area 59 of the integral back plate 50 extends between the rear ends of the posts 40. The intermediate area 59 is integral with the posts 40 and with the back plate 50. Thus, the whole magnetic core is formed by the monoblock 9.

The direction of lamination DL in the magnetic core 400 is such that it is parallel to the axis of rotation 10. It may be tolerated that the direction of lamination DL in the base plate 50 is not parallel with respect to the magnetic flow between the posts 40 in the base plate 50. It is also possible to manufacture the magnetic core 400 from coiled soft magnetic sheet material which is separated by electrically non-conducting layers. Then, the direction of lamination DL in the base plate 50 is always in the circumferential direction which is advantageous to avoid eddy currents in the magnetic flux in the base plate 50.

Figure 15A:
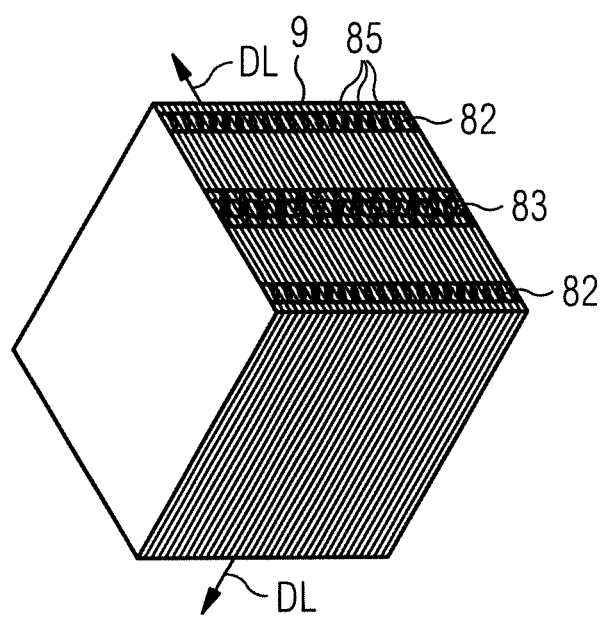
FIGS. 15A to 15C show how one or more welds may be provided on surfaces of the integrated magnetic core as manufactured according to FIGS. 14A to 14C.
Figure 15B:
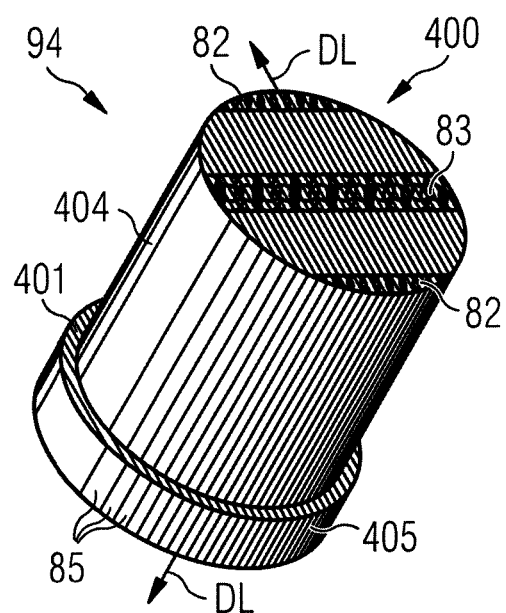
Figure 15C:
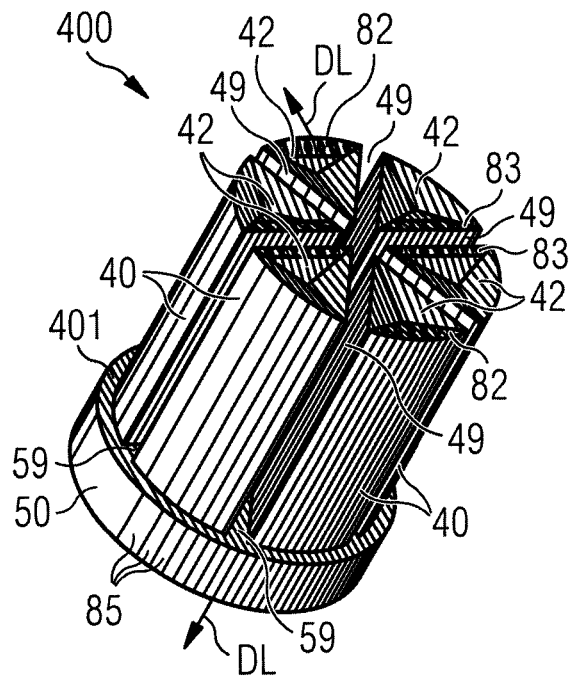

FIGS. 15A to 15C show how one or more welds may be provided on surfaces of the integrated magnetic core as manufactured according to FIGS. 14A to 14C. Accordingly, in the embodiment shown, three weld seams 82, 83 are provided on one side face of the cubical monoblock 9. The weld seams 82, 83 are welded at a distance to each other and across the cross section of the body 94 to be cut out of the monoblock 9. The weld seams 82, 83 run perpendicular to the direction of lamination DL of the sheets 85. In this way, the sheets of the discontinuous soft magnetic material are connected to each other. Instead of three weld seams, more weld seams or a single wider weld may be provided. In addition, similar weld seams may be provided on the opposite side of the monoblock 9 (not shown). Alternatively or in addition to the welds on the opposite side faces, one or more weld seams may be provided on a side surface of the monoblock 9 at the level of the back plate 50 so as to surround the back plate 50 completely or at least partially. The sheets 85 have a better mechanical connection to each other due to the weld seams 82, 83 and are also electrically connected. The latter has the advantage that electrical current can flow from any position of the discontinuous soft magnetic material to each position of electrical connection in the body 94 which may be required e.g. for electrical discharge machining. This way, electrical discharge machining is facilitated significantly. Furthermore, higher process reliability is achieved as the back plate-post unit to be cut-out of the body 94 cannot delaminate. Preferably, laser welding is applied. It may be advantageous to apply welding power to the same weld twice or even more often.

Subsequently, the body 94 is machined to form the magnetic core 400 as shown in FIG. 15C. In this second embodiment, the concavities in the front surfaces 42 of the posts 40 have three instead of two inclined side walls, all having downward inclination towards the center of the front surface. The outer circumference of the concavity coincides with the outer circumference of the front surface 42 of the post 40. However, the concavity is not open to any side surface of the post 40. Notably, the embodiment as shown in FIG. 14C with only two inclined side walls is more effective and, therefore, preferred.

The invention claimed is:

1. An intravascular blood pump for percutaneous insertion into a patient's blood vessel, comprising:
    a pump casing having a blood flow inlet and a blood flow outlet,
    an impeller arranged in said pump casing so as to be rotatable about an axis of rotation, the impeller having blades sized and shaped for conveying blood from the blood flow inlet to the blood flow outlet,
    a drive unit for rotating the impeller, the drive unit comprising a plurality of posts arranged about the axis of rotation, wherein each of the plurality of posts has an impeller-side end pointing towards the impeller with a front surface facing the impeller, and
    a coil winding disposed around each of the plurality of posts so as to create magnetic field lines running through the front surface of each of the plurality of posts and controllable so as to create a rotating magnetic field,
    wherein the impeller comprises a magnetic structure arranged to interact with the rotating magnetic field so as to cause rotation of the impeller, and
    wherein the front surface of at least one of the plurality of posts comprises a concavity in which the front surface is inclined downwards towards a central area of the front surface so as to concentrate at least a part of the magnetic field lines running through front surface, and
    wherein the concavity has a triangular cross section when viewed in a cross-sectional plane running vertically through the front surface.

2. The intravascular blood pump according to claim 1, wherein the concavity extends up to a circumference of the front surface.

3. The intravascular blood pump according to claim 2, wherein the concavity extends up to the circumference of the front surface on at least two or exactly two opposite sides of the front surface closest to neighboring ones of the plurality of posts.

4. The intravascular blood pump according to claim 2, wherein a circumference of the concavity coincides with the circumference of the front surface.

5. The intravascular blood pump according to claim 1, wherein the concavity has a flat bottom.

6. The intravascular blood pump according to claim 5, wherein the concavity has a straight-lined inclined side wall when viewed in a cross-sectional plane running vertically through the front surface.

7. The intravascular blood pump according to claim 5, wherein the concavity has a curved inclined side wall when viewed in a cross-sectional plane running vertically through the front surface.

8. The intravascular blood pump according to claim 1, wherein the concavity has a curved cross section with a curved bottom when viewed in a cross-sectional plane running vertically through the front surface.

9. The intravascular blood pump according to claim 1, wherein, in the concavity, the front surface is inclined downwards in a radially outer direction relative to the axis of rotation such that a radial inner region of the front surface in the concavity protrudes axially beyond a radial outer region of the front surface in the concavity.

10. The intravascular blood pump according to claim 1, wherein the concavity is open towards a side surface of said at least one of the plurality of posts, wherein the side surface is located radially outward relative to the axis of rotation.

11. The intravascular blood pump according to claim 10, wherein said at least one of the plurality of posts has three side surfaces, wherein one of the three side surfaces is located radially outward relative to the axis of rotation as compared to the other two of the three side surfaces and wherein the concavity is open towards the one of the three side surface.

12. The intravascular blood pump according to claim 1, wherein the concavity has a maximum depth of between 0.05 mm and 0.3 mm.

13. The intravascular blood pump according to claim 1, wherein the at least one of the plurality of posts has a longitudinal axis and does not extend with its impeller-side end radially beyond an impeller-side end of the coil winding disposed around the at least one of the plurality of posts, wherein radially is a direction at least transverse, up to and including perpendicular, to the longitudinal axis.

14. The intravascular blood pump according to claim 1, wherein at least one of the plurality of posts comprises a discontinuous soft magnetic material which is discontinuous regarding electrical conductivity in a cross section transverse to a longitudinal axis of the respective post.

15. The intravascular blood pump according to claim 14, wherein at least one weld is provided at a surface of the discontinuous soft magnetic material, the at least one weld bridging at least one discontinuity regarding electrical conductivity in the discontinuous soft magnetic material.

16. The intravascular blood pump according to claim 1, wherein each of the plurality of posts has a rear end, wherein the drive unit comprises a back plate connecting the rear ends of the plurality of posts and extending between the plurality of posts in an intermediate area, wherein a material of at least one of the plurality of posts is integral with a material of the intermediate area of the back plate.

17. The intravascular blood pump according to claim 1, wherein each of the plurality of posts has a rear end, wherein the drive unit comprises a back plate connecting the rear ends of each of the plurality of posts, wherein at least one of the rear ends of each of the plurality of posts has a rear end surface contacting the back plate.

\* \* \* \* \*

UNITED STATES PATENT AND TRADEMARK OFFICE
CERTIFICATE OF CORRECTION

PATENT NO. : 12,303,678 B2
APPLICATION NO. : 17/637264
DATED : May 20, 2025
INVENTOR(S) : Wolfgang Kerkhoffs et al.

It is certified that error appears in the above-identified patent and that said Letters Patent is hereby corrected as shown below:

In the Specification

Column 10, Line 20, Detailed Description:
Now reads: "spacer 7."; should read -- spacer 7. ¶ --

Column 11, Line 31, Detailed Description:
Now reads: "32"; should read -- 3 --

Column 12, Line 47, Detailed Description:
Now reads: "52"; should read -- 51 --

Column 15, Line 32, Detailed Description:
Now reads: "posts 40. ¶"; should read -- posts 40, --

Signed and Sealed this
Twenty-second Day of July, 2025

Coke Morgan Stewart
*Acting Director of the United States Patent and Trademark Office*